United States Patent [19]

Bornengo et al.

[11] Patent Number: 4,729,856

[45] Date of Patent: Mar. 8, 1988

[54] PROCESS FOR THE PREPARATION OF 2-PERFLUOROPROPOXY-PERFLUORO-PROPIONYL FLUORIDE

[75] Inventors: Giorgio Bornengo, Novara; Filippo M. Carlini, Vicenza; Michele Pontevivo, Novara; Giorgio Guglielmo, Gallarate, all of Italy

[73] Assignee: Ausimont S.p.A., Milan, Italy

[21] Appl. No.: 864,841

[22] Filed: May 20, 1986

[30] Foreign Application Priority Data

May 28, 1985 [IT] Italy ................... 20914 A/85

[51] Int. Cl.$^4$ ............................................. C07C 51/58
[52] U.S. Cl. ................................................. 260/544 F
[58] Field of Search ..................................... 260/544 F

[56] References Cited

U.S. PATENT DOCUMENTS 4,118,421 10/1978 Martini ........................... 260/544 F
4,390,720 1/1983 Resnick ............................ 560/184

FOREIGN PATENT DOCUMENTS 725740 1/1966 Canada ........................... 260/544 F Primary Examiner—Donald B. Moyer
Assistant Examiner—L. Hendriksen
Attorney, Agent, or Firm—Stevens, Davis, Miller & Mosher

[57] ABSTRACT

Process for the preparation of 2-perfluoropropoxy-perfluoropropionyl fluoride by dimerization of hexafluoropropene epoxide in aprotic polar medium, in the presence of N,N,N',N'-tetrasubstituted diaminodifluoromethane as catalyst, characterized in that the dimerization reaction is carried out in the presence of a co-catalyst constituted by a nitrogenous organic base having structure of aniline, or of pyridine, or of a derivative thereof, wherein the nitrogen atom is not linked to hydrogen atoms and, in the case of the pyridine-type structure, it is sterically hindered by substituent groups on ortho-position relatively to it.

5 Claims, No Drawings

PROCESS FOR THE PREPARATION OF 2-PERFLUOROPROPOXY-PERFLUOROPROPIONYL FLUORIDE

BACKGROUND OD THE INVENTION

1. Field of the Invention

The present invention relates to a process for the preparation of 2-perfluoropropoxy-perfluoropropionyl fluoride by dimerization of perfluoropropene epoxide (PFPO).

2. Description of the Prior Art

PFPO polymerization is known and disclosed in U.S. Pat. No. 3,322,826.

U.K. Pat. No. 1,550,268 discloses the preparation of PFPO oligomers in aprotic polar solvent at temperatures of from $-50°$ C. to $+20°$ C. in the presence of N,N,N',N'-tetrasubstituted diaminodifluoromethane as catalyst; oligomers are obtained which can be represented by the following general formula:

$$R_F-O-(-CF(CF_3)-CF_2-O)_n-CF(CF_3)-C(=O)F$$

wherein $R_F$ represents a perfluoroalkyl chain containing from 1 to 8 carbon atoms, and n ranges from 0 to 4.

According to this patent, it is recommended to operate by carefully controlling the reaction temperature because, in order to obtain high yields in dimer, due to the low boiling point of PFPO ($-29°$ C.), maintaining the temperature within the range of from $0°$ C. to $20°$ C. with high PFPO concentrations and under increased pressure is necessary. The reaction times result however to be rather long, of the order of 24 hours. The trimers, tetramers and pentamers are obtained on the contrary by operating at temperatures comprised within the range of from $-15°$ C. to $-30°$ C., under atmospheric pressure and with low PFPO concentrations.

THE PRESENT INVENTION

It has been now surprisingly found that high yields in PFPO dimer are obtained within a wide temperature range and with very short reaction times, of the order of 4 hours, if the dimerization, carried out in an aprotic polar solvent to which an N,N,N',N'-tetrasubstituted diaminodifluoromethane as catalyst has been added, is carried out in the presence of a suitable co-catalyst.

The object of the present invention is hence a process to obtain, with high yields, and within very short reaction times, the product represented by the following structural formula:

$$CF_3CF_2CF_2-O-CF(CF_3)-C(=O)F$$

(2-perfluoropropoxy-perfluoropropionyl fluoride).

Further object of the present invention is to provide a process suitable to be easily accomplished on full industrial scale, and which is flexible and not rigorously bound to such physical parameters as temperature and pressure.

According to the present invention, the dimerization reaction is carried out at temperatures comprised within the range of from $-50°$ C. to $+50°$ C., preferably of from $-40°$ C. to $+20°$ C. in aprotic polar solvent, wherein the catalyst constituted by the N,N,N',N'-tetrasubstituted diaminodifluoromethane is dissolved, and in the presence of a co-catalyst.

The co-catalyst of the invention is constituted by an organic nitrogenous base and is represented by the following general formulae:

[Structure 1: benzene ring with $R_5, R_6$ on N substituent and $X_1, X_2, X_3$ on ring]

[Structure 2: pyridine ring with $R_7, X_4, X_5, R_8, R_9$ substituents]

wherein $R_5$, $R_6$, $R_8$ and $R_9$, equal to or different from each other, are a hydrocarbon radical containing from 1 to 8 carbon atoms, which can either contain or not contain a substituent group inert towards the reactants under the reaction conditions; $R_7$ can be also H; $R_7$ and $R_8$ can furthermore be linked to each other to form a second five- or six-membered ring and which can be either aliphatic or aromatic;

$X_1$, $X_2$, $X_3$, $X_4$ and $X_5$, equal to or different from each other, can be H, halogen or a hydrocarbon radical of from 1 to 8 carbon atoms, which can either contain or not contain a substituent group inert towards the reactants under the reaction conditions.

Organic nitrogenous bases which can be conveniently used comprise: N,N-dimethylaniline, N,N-diethylaniline, 2,6-dimethylpyridine, 2,6-di-tert.butylpyridine, 4-propyl-2,6-dimethylpyridine.

The co-catalyst is used in amounts comprised within the range of from 0.001 to 10, preferably from 0.01 to 0.5, mol/PFPO mol.

The N,N,N',N'-tetrasubstituted diaminodifluoromethane used as the catalyst in PFPO dimerization is described in U.K. Pat. No. 1,550,268 and is a compound having the following general formula:

$$R_1R_2N-CF_2-NR_3R_4$$

wherein $R_1$, $R_2$, $R_3$, $R_4$ are equal to or different from each other and each of them represents an alkyl radical of from 1 to 4 carbon atoms. Moreover, the two radicals bound to a same nitrogen atom can form, together with the same nitrogen atom, five- or six-membered rings which can also have one carbon atom replaced by one of the following atoms or groups:

$$-O-,\quad \text{N}-(C_1-C_4) \text{ or } \text{N}-CF_2H$$

Preferably, the radicals represented by $R_1$, $R_2$, $R_3$ and $R_4$ are alkyl radical of from 1 to 2 carbon atoms and moreover both $R_1$ and $R_2$, and $R_3$ and $R_4$ can form, together with the nitrogen atom they are linked to, pyrrolidinyl, piperidinyl, N-methylpiperazinyl or morpholinyl radicals.

The catalyst can be advantageously prepared in situ in the reaction mixture by starting from the corresponding urea or thiourea.

The catalyst is used in amounts comprised within the range of from 0.001 to 10, preferably of from 0.01 to 0.5, mol/PFPO mol.

In the catalytic system according to the present invention, the co-catalyst to catalyst molar ratio is preferably comprised within the range of from 5:1 to 5:1.5.

Aprotic polar solvents which can be advantageously used in the dimerization can be ethers, such as diethyleneglycol dimethylether, tetraethyleneglycol dimethylether, diethyleneglycol diethylether, and nitriles, such as acetonitrile and propionitrile, or dimethylformamide. Furthermore, the polar solvent can be diluted with an apolar inert solvent of aliphatic or cycloaliphatic hydrocarbon character such as pentane, hexane, cyclohexane, or with an aliphatic halocarbon, such as trichloroethane or trifluorotrichloroethane, without substantial changes in reaction proceeding.

The amount of solvent is not critical, because both the dimer and the possible higher oligomers of PFPO are insoluble in the aprotic polar solvent used, and separate from the reaction solution forming a second phase generally heavier than the previous one.

The solvent is generally used in amounts comprised within the range of from 10 to 200 ml and preferably of from 10 to 100 ml/100 g of PFPO used.

A preferred operating way consists in dissolving both the catalyst and the co-catalyst in the aprotic polar solvent, the mixture being subsequently cooled to a temperature comprised within the range of from $-30°$ C. to $-40°$ C. PFPO (which can be either pure or in mixture with perfluoropropene (PFP) in the liquid state) is then added.

The mixture is kept stirred for, e.g., four hours at a temperature comprised within the range of from $-50°$ C. to $+50°$ C.

At the end of the reaction, the lower phase is separated and from it, by distillation, the dimer is separated from the higher PFPO oligomers (mainly PFPO trimer and tetramer). The conversion is of the order of 98% and the selectively to dimer can be as high as 80%.

The reaction pressure and temperature are parameters not critical to the dimerization; operating at temperatures of from $-40°$ C. to $+20°$ C. and under such a pressure as to keep PFPO in liquid phase at the reaction temperature is preferred.

The results achieved by the present invention are much more surprising because it was totally unexpected that the addition of the co-catalyst of the invention to N,N,N',N'-tetrasubstituted diaminodifluoromethane would allow PFPO to react with high yields to dimer within shorter reaction times, of the order of four hours, than the very long times of the prior art, and within a much wider temperature range.

In fact, the addition of other bases which do not have the characteristics of the bases of the invention, such as, e.g., non-disubstituted anilines or aliphatic amines, also tri-substituted, does not lead to any advantages as compared to the processes used in the prior art, as described hereinabove.

The amines of the invention perform their selectivity only in the presence of the N,N,N',N'-tetrasubstituted diaminodifluoromethane, giving rise to a specific catalytic system active as regards the dimerization within a wide temperature range of from $-50°$ C. to $+50°$ C., thus allowing the most suitable operating conditions for a full scale industrial production to be selected, and the reaction to occur within very short times, of the order of 4 hours.

The following Examples are given to the only purpose of illustrating the invention, and must not be considered as being limitative of the same invention.

EXAMPLE 1

One hundred grams of a gaseous mixture, constituted by 80 g of perfluoropropene epoxide (PFPO) (0,482 mol) and 20 g of perfluoropropene (PFP) is liquified at $-40°$ C. and introduced into a 1-liter reaction vessel provided with a jacket through which a refrigerating mixture is forcedly circulated, equipped with reflux condenser to prevent the escape of the reactants vapours, thermometer, stirrer, and valve for PFPO feed, preliminarily cooled to $-40°$ C., said reactor containing 45 ml of acetonitrile, 1.89 g of N,N,N',N'-tetramethylurea (0.0163 mol) and 9.49 g of N,N-dimethylaniline (0.0784 mol).

At the end of the introduction, the temperature is raised to $-30°$ C. and the mixture is kept under strong stirring for 4 hours.

At the end of the reaction, PFP is distilled off at room temperature directly from the reactor and then, from the liquid residue, the lower phase is separated and distilled separately.

After the distillation:

59 g of dimer $(PFPO)_2$ 16 g of trimer $(PFPO)_3$ 4 g of tetramer $(PFPO)_4$ are obtained.

The conversion is of 99% and the selectivity to dimer is of 75%.

COMPARATIVE EXAMPLE 2

Example 1 is repeated, by using the same modalities and the same amounts of reactants and of catalyst, but without adding the co-catalyst constituted by N,N-dimethylaniline.

At the end of the reaction, PFP is distilled off and then, from the liquid residue, the lower phase is separated. This latter is distilled:

7 g of dimer $(PFPO)_2$ 49 g of trimer $(PFPO)_3$ 23 g of tetramer $(PFPO)_4$ being obtained.

The conversion is of 99% and the selectivity to dimer is of 9%.

EXAMPLE 3

One hundred and twenty grams of a gaseous mixture, constituted by 96 g of PFPO (0,578 mol) and 24 g of PFP is liquified at $-40°$ C. and introduced into an 1-liter steel autoclave provided with a jacket with forced circulation of refrigerating mixture, equipped with thermometer, stirrer, pressure gauge and valve for PFPO feed, preliminarily cooled to $-40°$ C., said autoclave containing 53 ml of acetonitrile, 2.26 g of N,N,N',N'-tetramethylurea (0.0195 mol) and 11.3 g (0.0938 mol) of N,N-dimethylaniline.

The temperature is raised to $+20°$ C. over a time of 1 hour and 30 minutes and the mixtures is kept under stirring for an overall time of 4 hours.

At the end of the reaction, PFP is distilled off and then, from the liquid residue, the lower phase is separated and distilled separately.

After the distillation:
75 g of dimer (PFPO)$_2$
16 g of trimer (PFPO)$_3$
2 g of tetramer (PFPO)$_4$
are obtained.

The conversion is of 97% and the selectivity to dimer is of 81%.

EXAMPLES 4-9

A series of dimerization reactions are carried out by using the same amounts of reactants, of catalyst, and of solvent as of Example 1, but different co-catalysts, all of them being used in an amount corresponding to 0.08 mol.

The tests of Examples 4, 6, 7, 8 are carried out by using the same equipment as of Example 1, and following the same operating procedure as described in said Example.

The tests of Examples 5 and 9 are carried out by using the same equipment as of Example 3, and following the same operating procedure as described in said Example.

The conversion, the selectivity to dimer and the temperature of each test are reported in the following Table.

TABLE

| Example | Co-Catalyst | Reaction Temperature | Conversion | Selectivity |
|---|---|---|---|---|
| 4 | N,N—diethylaniline | −30° C. | 97 | 77 |
| 5 | N,N—diethylaniline | +20° C. | 97 | 79 |
| 6 | 4-Br—N,N—dimethylaniline | −30° C. | 97 | 74 |
| 7 | 2,6-dimethylpyridine | −30° C. | 98 | 71 |
| 8 | 2,6-ditert.butylpyridine | −30° C. | 98 | 73 |
| 9 | 2-methylquinoline | +20° C. | 97 | 74 |

EXAMPLE 10

Example 1 is repeated, but using 0.08 mol of 2,6-dimethylpyridine as the co-catalyst and 45 ml of diethyleneglycol dimethylether as the solvent.

A conversion of 97% and selectivity to dimer of 73% is obtained.

EXAMPLE 11

Example 1 is repeated, but using 0.08 mol of 2,6-di-tert.butylpyridine as the co-catalyst and a mixture constituted by 30 ml of diethyleneglycol dimethylether and 20 ml of trifluorotrichloroethane as the solvent.

A conversion of 98% and selectivity to dimer of 74% is obtained.

COMPARATIVE EXAMPLE 12

One hundred and twenty grams of a gaseous mixture, constitued by 96 g of PFPO (0,578 mol) and 24 g of PFP is liquified at −40° C. and introduced into a reactor equal to that of Example 1, preliminarily cooled to −40° C., and containing 55 ml of diethyleneglycol dimethylether and 15 g of 2,6-di-tert.butylpyridine (0.078 mol).

At the end of the introduction, the temperature is raised to −30° C. and the mixture is kept stirred for 4 hours.

Under these conditions, not any oligomerization reactions occur, and the initial gas mixture is recovered.

COMPARATIVE EXAMPLE 13

One hundred grams of a gaseous mixture, constituted by 80 g of PFPO and 20 g of PFP is liquified at −40° C. and introduced into a reactor equal to that of Example 1, preliminarily cooled to −40° C. and containing 45 ml of acetonitrile and 8 g of triethylamine.

At the end of the introduction, the temperature is raised to −30° C. and the mixture is kept stirred for 4 hours.

Under these conditions, not any oligomerization reaction occur, and the initial gas mixture is recovered.

COMPARATIVE EXAMPLE 14

Example 1 is repeated, by following the same operating modalities and using the same amounts of reactants and of catalyst, but replacing the co-catalyst with an equal molar amount of triethylamine. At the end of the reaction, PFP is distilled off and then, from the liquid residue the lower phase is separated.

This latter is distilled,
6 g of dimer (PFPO)$_2$
47 g of trimer (PFPO)$_3$
20 g of tetramer (PFPO)$_4$
being obtained.

A conversion of 91% as referred to the oligomers is obtained.

The selectivity to dimer is of 8%.

What is claimed is:

1. Process for the preparation of 2-perfluoropropoxyperfluoropropionyl fluoride by dimerization of perfluoropropene epoxide in an aprotic polar solvent selected from the group consisting of ethers, nitriles and dimethylformamide, at temperatures comprised within the range of from −50° C. to +50° C., in the presence of a catalyst comprising an N,N,N',N'-tetrasubstituted diaminodifluoromethane and a co-catalyst comprised within the following formulae:

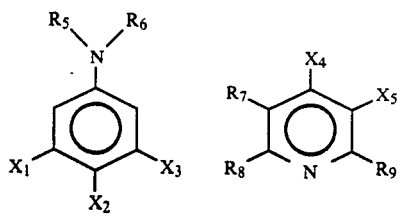

wherein $R_5$, $R_6$, $R_7$, $R_8$, and $R_9$, equal to or different from each other, are a hydrocarbon radical containing from 1 to 8 carbon atoms, which can either contain or not contain a substituent group inert towards the reactants under the reaction conditons; $R_7$ can be also H; $R_7$ and $R_8$ can furthermore be linked to each other to form a second ring of 5 or 6 carbon atoms and which can either aliphatic or aromatic; $X_1$, $X_2$, $X_3$, $X_4$, and $X_5$, equal to or different from each other, can be H, halogen or a hydrocarbon radical of from 1 to 8 carbon atoms, which can either contain or not contain a substituent group inert towards the reactants under the reaction conditions, said co-catalyst being used in amounts comprised within the range of from 0.001 to 10 mol/perfluoropropene epoxide mol.

2. Process according to claim 1, wherein said co-catalyst is used in amounts comprised within the range of from 0.01 to 0.5 mol/perfluoropropene epoxide mol.

3. Process according to claim 1, wherein the co-catalyst/catalyst molar ratio is comprised within the range of from 5:1 to 5:1.5.

4. Process according to claim 1, carried out at temperatures comprised within the range of from −40° C. to +20° C.

5. Process according to claim 1, wherein the solvent is used in amounts comprised within the range of from 10 to 200 ml/100 g of perfluoropropene epoxide.

* * * * *